United States Patent
Isele

(10) Patent No.: US 8,628,794 B2
(45) Date of Patent: Jan. 14, 2014

(54) PALATABLE DUCTILE CHEWABLE VETERINARY COMPOSITION

(75) Inventor: Ute Isele, Freiburg (DE)

(73) Assignee: Novartis AG, Basel (CH)

( * ) Notice: Subject to any disclaimer, the term of this patent is extended or adjusted under 35 U.S.C. 154(b) by 1533 days.

(21) Appl. No.: 10/564,339

(22) PCT Filed: Jul. 29, 2004

(86) PCT No.: PCT/EP2004/008538
§ 371 (c)(1),
(2), (4) Date: Jan. 11, 2006

(87) PCT Pub. No.: WO2005/013714
PCT Pub. Date: Feb. 17, 2005

(65) Prior Publication Data
US 2006/0222684 A1    Oct. 5, 2006

(30) Foreign Application Priority Data

Jul. 30, 2003 (EP) .................................. 03017252

(51) Int. Cl.
| | |
|---|---|
| A61K 9/28 | (2006.01) |
| A61K 31/335 | (2006.01) |
| A61K 31/34 | (2006.01) |
| A61K 9/00 | (2006.01) |
| A23K 1/00 | (2006.01) |
| A23K 1/18 | (2006.01) |
| A23K 1/17 | (2006.01) |

(52) U.S. Cl.
USPC ............... 424/441; 424/400; 424/442; 426/2; 514/450; 514/461; 514/462

(58) Field of Classification Search
USPC ............... 424/442, 400, 441; 426/2; 514/450, 514/461, 462
See application file for complete search history.

(56) References Cited

U.S. PATENT DOCUMENTS

| | | | |
|---|---|---|---|
| 4,284,652 A | 8/1981 | Christensen | |
| 4,393,085 A | 7/1983 | Spardlin et al. | |
| 4,707,375 A | 11/1987 | Buckley et al. | |
| 5,262,167 A | 11/1993 | Vegesna et al. | |
| 5,605,889 A | 2/1997 | Curatolo et al. | |
| 5,637,313 A | 6/1997 | Chau et al. | |
| 5,824,336 A | 10/1998 | Gilis et al. | |
| 5,958,445 A | 9/1999 | Humber et al. | |
| 6,500,463 B1 | 12/2002 | Van Lengerich | |
| 6,653,342 B2 | 11/2003 | Saito et al. | |
| 6,866,862 B2 | 3/2005 | Huber et al. | |
| 7,052,712 B2 | 5/2006 | Huber et al. | |
| 2001/0036464 A1 | 11/2001 | Christensen | |
| 2004/0043925 A1 | 3/2004 | Kalbe et al. | ........................ 514/9 |

FOREIGN PATENT DOCUMENTS

| | | | |
|---|---|---|---|
| CA | 2257547 | 7/1999 | |
| CA | 2413698 A1 * | 12/2002 | ............... A61K 9/20 |
| DE | 198 53 729 | 3/2000 | |
| EP | 1 247 456 | 10/2002 | |
| GB | 2 190 093 A | 11/1987 | |
| GB | 2 300 103 | 10/1996 | |
| JP | 11/269098 A | 5/1999 | |
| WO | WO 99/48372 | 9/1999 | |
| WO | WO00/13521 | 3/2000 | |
| WO | WO 03/030653 | 4/2003 | |
| WO | 2004016252 | 2/2004 | |
| WO | WO 2004/014143 A1 | 2/2004 | |
| WO | WO 2004/016252 | 2/2004 | |

* cited by examiner

Primary Examiner — Sue Liu
Assistant Examiner — Andriae M Holt
(74) Attorney, Agent, or Firm — Ann R. Pokalsky, Esq.; Dilworth & Barrese, LLP

(57) ABSTRACT

The present invention is directed to palatable ductile chewable veterinary composition for oral administration. The composition is capable of killing endo-parasites and ecto-parasites and/or can be used for treating prophylactic or curative animal diseases, and it is useful for the treatment of any warm-blooded non-human animal, including herd animals, like horses, cattle, sheep or poultry and preferably pets like dogs and cats. It consists basically of (A) an effective amount of one or more ingredients that are active against animal pests, pathogens or animal diseases; (B) meat flavoring; (C) partially gelatinized starch; (D) a softener; and (E) up to 9% water.

13 Claims, No Drawings

PALATABLE DUCTILE CHEWABLE VETERINARY COMPOSITION

This application is a National Phase Application under §371 of International Application Number PCT/EP2004/008538 filed on Jul. 29, 2004.

The present Invention relates to an easy-to-use, safe, efficacious, and stable veterinary formulation consisting of a highly palatable ductile chewable veterinary composition comprising an effective amount of one or more ingredients that are active against animal pests, pathogens or animal diseases; of meat flavoring; of partially gelatinized starch; of a softener; and of up to 9% of water. The present invention also relates to a method of controlling said animal pests or pathogens and of curing or preventing said animal diseases by feeding an animal with said highly palatable ductile chewable veterinary composition. Further, the invention relates to a process for producing said highly palatable ductile chewable veterinary composition by cold extrusion. In a preferred embodiment, the highly palatable ductile chewable veterinary composition controls animal pests like endo-parasites, such as worms, and simultaneously ecto-parasites, such as biting insects like fleas, on pets. The pesticidally effective Ingredient is dispensed as the animal chews the product.

FIELD AND BACKGROUND OF THE INVENTION

Veterinary products can be administered to warm-blooded animals in very different ways depending on their mode of action and their ability to be taken up either by the treated animal or the target pest. Thus veterinary products can be administered, for example, topically as pour-on or spot-on formulations, in form of shampoos, showers, as a dip, bath or spray, in form of a collar, and in many variants of these application forms. They can also be administered systemically, for example, orally, parenterally and in certain cases even transdermally. Examples of systemic administration forms are: via injection, as a tablet, capsule, bolus, drink, feed additive and the like. Each of these administration forms can have advantages or disadvantages depending on the actual situation and the animal that is in need of such a treatment. Treatment of herd animals, like horses, cattle, sheep or poultry usually requires different administration methods than for the treatment of single animals, such as pets like dogs and cats.

One very convenient and easy to manage administration form for human patients is the oral uptake of a medicament. This would also be very desirable in the field of veterinary medicine but here the animal holder or veterinarian is confronted with the natural behavior of the animal and oral treatment can be a real challenge.

Many attempts have been made to design the ideal oral application form that is really accepted and voluntarily taken up by the animal but most of these application forms need still to be improved.

The present inventors recognized that in the field of animal health the dosage form and especially the palatability of the dosage form, i.e. the natural acceptance of the drug plays the decisive role. The underlying problems are outlined hereinafter.

While, in humans, medicaments may be administered in a wide variety of application forms, such as tablets, coated tablets, emulsions, injection solutions, suppositories and the like, because the discipline and the desire to recover in human patients can be relied upon, in the case of animals practical problems are soon encountered, since a few application forms, such as the usage of suppositories, either have to be dispensed with all together or other forms, such as injections, must only be carried out by the veterinarian.

In general, humans do not like to visit the doctor. The same is true for animal keepers who would need advice from a veterinarian. In general, the animal keeper prefers to use those treatment methods that he can carry out himself without having involved a veterinarian. Among the preferred treatment methods, which an animal keeper can carry out himself, e.g. following the veterinarian's instructions, is the oral administration of medicaments.

Treating humans with medicines is generally not problematic, because the human patient follows the advice of the doctor or reads the directions on the leaflet in the package and complies with them since this is in his own interest, and because the manufacturer usually prepares the tablet, capsule or coated tablet in a form which is appropriate for oral consumption and has been tailored for human patients.

However, as soon as a pharmaceutical active ingredient has a taste which is unpleasant to the animal, whether because it is bitter or has some other unpleasant taste or is simply alien to the animal, the animal refuses to take it orally. This inborn behavior occurs to varying degrees among the different species of animals, and essentially depends on their conventional eating habits. Unfortunately, only a few active ingredients have a neutral taste, so that the problem being discussed here is almost always present.

In the case of a human patient, an unpleasant tasting active ingredient can be masked relatively easily, e.g. by coating it with a neutral-tasting or sweet layer. Everybody has come across gelatin capsules or tablets coated with sugar or lacquer at some time or other. It is easy to instruct the human patient to take the preparation without chewing.

An animal must have a natural willingness to take a medicinal preparation orally, which means that the medical preparation must taste well and be palatable. Of course, an individual animal or a few animals can also be forced to take a medicament, by making it swallow or by injecting it. However, such forced methods are not only unacceptable to large animal operations but also to single dogs and cats which tend to bite or scrape if they are not willing to be treated. This is why animal treatment can be very labor-intensive or can require the intervention of a veterinarian and this ultimately leads to increase of costs.

Therefore, for pets but equally for animals that are kept on a large scale, simple and safe oral application forms are required, which can be easily administered by the animal keeper, which lead to reliable results, and which are affordable.

The chewable composition according to the present invention is not only suitable for replacing the treatment with a tablet or capsule. These chewables can also easily be mixed with conventional non-medicated feed pellets if herds of animals have to be treated.

Due to their excellent palatability the chewables according to the present invention are taken up by animals without causing any acceptance problems. Their handling is easy and safe, and can be adapted to the need either of an individual animal like a cat or a dog or to a herd animals like sheep and cows.

When reviewing the administration of capsules and coated tablets to animals, it has been shown that these application forms are rather unsuitable for animal medicine, since in the case of herd animals they can only be used in a controlled manner with considerable effort on a daily basis, and in the case of pets, such as dogs and cats, lead to particular acceptance problems. As already mentioned above, the eating habits of animals generally play a decisive role when using oral application forms. Thus, most important is an attractive taste and the palatability.

In the case of dogs, it has been observed that they gnaw at solid food, e.g. on bones, and gulp down other food, either in the form of large scraps or wet formulated food, almost unchewed. If a tablet or coated tablet is mixed with the wet formulated feed, varying results are obtained. In a few cases, the tablet is not noticed by the dog at all and is simply gulped down, and in other cases it remains uneaten in the dog bowl. In contrast to dogs, cats are considerably more fastidious in their eating habits. Only in the rarest cases can a tablet or coated tablet be mixed with the formulated food, without them noticing it immediately and rejecting it. Although cats also to not exactly chew their food, they generally break it down with a few small bites. They thereby damage the protective coating of a tablet or capsule and release the unpleasant tasting active ingredient. Attempts to mix the active ingredient directly with the feed likewise fail, because either the degree of dilution is insufficient to neutralize the unpleasant taste or the active ingredient breaks down too rapidly when in contact with the feed. For the same reasons, mixtures of feed, active ingredient and excipients, which should stimulate the appetite of dogs and cats, similarly do not have a successful outcome with cats. Whereas the test animals rush eagerly to a placebo which has a corresponding appetite stimulant, i.e. a tablet consisting of feed, flavoring and other excipients, but no active ingredient, the test animals reject the same combination as soon as active ingredient is added. Clearly, a different technical solution must be found to the existing problem with animals.

Of course, any other active ingredient which is suitable for animals can be administered according to the present invention, but especially those active ingredients that have the taste disadvantages mentioned initially and are therefore not willingly taken orally by animals.

Basically, a diversity of individual active ingredients or mixtures of active ingredients may be considered, e.g. those acting against external (ecto) or internal (endo) parasites or active ingredients acting against animal diseases including viral or bacterial infections, behavioral disorders, such as hypo- or hyper-activity, inflammatory diseases, and autoimmune diseases. Thus, the active ingredient can be a pesticide or a medicament or a mixture of both.

It should be kept in mind that the present invention deals with an optimized application form for veterinary compositions rather than with the treatment of animals with a specific class of active ingredients. On the contrary, the present invention provides an easy-to-use, safe, powerful, and stable veterinary formulation consisting of a highly palatable ductile chewable veterinary composition, which allows to administer orally almost each and any active ingredient to a warm-blooded animal, provided that this active ingredient or mixture of active ingredients is at the administered dose physiologically acceptable to the animal, does not display unacceptable side effects and, what is most important, exhibits after oral uptake systemic activity. This means that the main prerequisite for the active ingredient is that after oral administration it is taken up by the body fluids, including blood and lymph, and transported to the animal pest, the pathogen or the diseased organ where it can exhibit its activity. Thus, any active ingredient or class of active ingredients mentioned hereinafter is nothing but a non-limiting example of suitable active ingredients. The application form of the present invention is actually not limited to existing active ingredients but also suitable for each and any active ingredient developed in the future provided that the future active ingredient meets the main characteristics explained hereinbefore.

The highly palatable ductile chewable veterinary composition of the present invention is in principle a medicated food product and everybody working in this area is aware of the technical problems that arise in context with the production of medicated feed. For example, stability of the active ingredient is very crucial. It is a matter of fact that many potent active compounds are somewhat unstable (temperature-sensitive), above all when in contact with feed material, especially close contact to vegetable and animal materials, during conventional extrusion of feed pellets, result in considerable losses of active ingredient.

For example, when feed pellets are prepared via extrusion, the dried organic starting material of animal or vegetable origin is ground, is intimately mixed with the active ingredient, that is to say is substantially homogenized, and then is moistened with water or steam and is compressed into pellets at elevated temperatures and under pressures of around 100 kbar. However, said high pressures and the permanent high temperatures in the range of 60-100° C. are disadvantageous and do not only dramatically reduce the viscosity of the pellets but result in a considerable lost of active ingredient.

Whereas most active ingredients in pure form or in contact with carriers that are routinely used in the production of tablets or capsules withstand such relatively high temperatures per se very well and can be stored in pure form or as tablets or capsules at room temperature for months or years without any measurable loss of active ingredient, they decompose relatively rapidly under pressure and in intimate contact with animal or vegetable fibers in feedstuffs and under the prevailing elevated temperatures. It appears that contact with the fibers actually catalyses the decomposition process. Even when the elevated-pressure and elevated-temperature phase is kept as short as technically possible and the finished pellets are immediately cooled down to room temperature directly after the compression process, a quarter to a third of the active ingredient is nevertheless lost. Even though in the rare cases where the degradation products do not have disadvantageous effects on the animals treated, the unavoidable loss of active ingredient inevitably results in a considerable increase in the cost of the final product. Thus extrusion processes can lead to very undesirable effects.

For the reasons mentioned, therefore, much effort has been directed at stabilizing temperature-sensitive active ingredients so that they withstand the elevated temperatures and pressures during pellet preparation without loss of active substance and also, when in the form of the finished pellets, have a long-term storage stability suitable for practical purposes.

Unsuccessful attempts at such stabilization include, for example, (1) reduction of the active ingredient surface area by means of compression into granules, a very great variety of granule sizes having been tried; (2) sealing of the said active ingredient granules in a very great variety of protective layers, for example gelatin or various sugars and coatings; (3) enclosure of the active ingredient within porous materials such as, for example, various celluloses, starches, silicic acids or zeolites, with or without additional protective layers; and (4) chemical modification of the basic macrocyclic structure of the active ingredient. Although in a few cases chemical modification has resulted in improved stability of the compound per se, it has simultaneously resulted in loss of activity.

However, none of those attempts has resulted in an appreciably smaller loss of active ingredient on compression into feed pellets or in measurably improved storage stability.

Moreover, success has now been achieved, surprisingly, in providing the user with the user-friendly, easy-to-use, safe, powerful, stable, and especially highly palatable chewable veterinary composition of the present invention.

Astonishingly, it is now possible to provide a product that not only withstands the extrusion process undamaged but also survives for a outstanding long storage period.

Therefore, it is highly surprising and was absolutely unpredictable that even so the chewable veterinary composition of the present invention contains a relatively high amount of meat material, this has obviously when combined with the appropriate amount of partially gelatinized starch, no adverse effect on the stability of the active ingredient. It actually turned out that the chewable veterinary composition of the present invention is a very stable product that can be stored at room temperature over many months without significant loss or degradation of active ingredient. Tests with stored material demonstrate that the palatability is not decreased and the efficacy of the active ingredient stays at a high level.

Moreover, investigations of the kinetic behavior demonstrate another surprising effect. It could not have been foreseen that the administration of the chewable veterinary composition of the present invention could lead to absolutely the same level of bioavailability as the administration of tablets or capsules. Thus, the present invention provides a safe, easy to use and stable product that is at least as efficacious as conventional oral application forms, like tablets or capsules.

Many biocides and veterinary medicines that may be now be incorporated into the chewable veterinary composition and be used according to the present invention, have been known to skilled specialists for a long time but the conventional oral dosage forms are not satisfactory because they are not attractive for animals and show the disadvantages discussed above.

With the chewable veterinary composition of the present invention one can combat all kinds of parasites. External parasites, also called ecto-parasites, are understood to be parasites which normally live on the animal, i.e. an the animal's skin or in the fur. Enclosed are biting insects, such as mosquitoes, blowfly, fleas or lice, or members of the order Acarina, e.g. mites or ticks. Suitable products against external parasites include insecticides and acaricides. It does not matter what their mode of action actually is. They can be e.g. chitin synthesis inhibitors, growth regulators; juvenile hormones; adulticides. They can be broadband insecticides, broad-band acaricides. The active ingredient can be a killer or a deterrent or repellent. It can affect e.g. only adult stages or juvenile stages of the parasite or may affect any stage. The only prerequisite is that the active ingredient acts systemically. This means that it is not decomposed after oral uptake but transported by the body fluids to the skin or organ where the parasite uses to live.

If the active ingredient is an acaricide one can, for example, select a systemically acting acaricide from one of the following well-known classes of acaricides including: antibiotic acaricides such as abamectin, doramectin, eprinomectin, ivermectin, milbemectin, nikkomycins, selamectin, tetranactin, and thuringiensin; bridged diphenyl acaricides such as azobenzene, benzoximate, benzyl benzoate, bromopropylate, chlorbenside, chlorfenethol, chlorfenson, chlorfensulphide, chlorobenzilate, chloropropylate, dicofol, diphenyl sulfone, dofenapyn, fenson, fentrifanil, fluorbenside, proclonol, tetradifon, and tetrasul; carbamate acaricides such as benomyl, carbanolate, carbaryl, carbofuran, fenothiocarb, methiocarb, metolcarb, promacyl, and propoxur; oxime carbamate acaricides such as aldicarb, butocarboxim, oxamyl, thiocarboxime, and thiofanox; dinitrophenol acaricides such as binapacryl, dinex, dinobuton, dinocap, dinocap-4, dinocap-6, dinocton, dinopenton, dinosulfon, dinoterbon, and DNOC; formamidine acaricides such as amitraz, chlordimeform, chloromebuform, formetanate, and formparanate, mite growth regulators such as clofentezine, dofenapyn, fluazuron, flubenzimine, flucycloxuron, flufenoxuron, and hexythiazox; organochlorine acaricides such as bromocyclen, camphechlor, dienochlor, and endosulfan; organotin acaricides such as azocyclotin, cyhexatin, and fenbutatin oxide; pyrazole acaricides such as acetoprole, Fipronil and analogues and derivatives thereof, tebufenpyrad, and vaniliprole; pyrethroid acaricides including: pyrethroid ester acaricides like acrinathrin, bifenthrin, cyhalothrin, cypermethrin, alphacypermethrin, fenpropathrin, fenvalerate, flucythrinate, flumethrin, fluvalinate, tau-fluvalinate, and permethrin, and pyrethroid ether acaricides like halfenprox; quinoxaline acaricides such as chinomethionat and thioquinox; sulfite ester acaricides such as propargite; tetronic acid acaricides such as spirodicofen; and from unclassified acaricides such acequinocyl, amidoflumet, arsenous oxide, chloromethiuron, closantel, crotamiton, diafenthiuron, dichlofluanid, disulfiram, fenazaflor, fenazaquin, fenpyroximate, fluacrypyrim, fluenetil, mesulfen, MNAF, nifluridide, pyridaben, pyrimidifen, sulfiram, sulfluramid, sulfur and triarathene.

Suitable insecticides acting either as adulticides or insect growth regulators (IGRs) can be chosen from a variety of well-known different chemical classes such as chlorinated hydrocarbons, organophosphates, carbamates, pyrethroids, formamidines, borates, phenylpyrazoles, and macrocyclic lactones (previously known as avermectins). Prominent representatives of adulticides/insect killers are imidacloprid, fenthion, fipronil, allethrin, resmethrin, fenvalerate, permetrin, malathion and derivatives thereof. Insect adulticides kill the insect in almost any development stage either by contact or as a stomach poison. Widely used representatives of insect growth regulators (IGRs) are, for example benzoylphenylureas such as diflubenzuron, lufenuron, noviflumuron, hexaflumuron, triflumuron, and teflubenzuron or substances like fenoxycarb, pyriproxifen, methoprene, kinoprene, hydroprene, cyromazine, buprofezin, pymetrozine and derivatives thereof. Insect growth inhibitors or insect growth regulators (any of which is commonly known as an IGR) are products or materials that interrupt or inhibit the life cycle of a pest.

It goes without saying that the highly palatable ductile chewable veterinary composition according to the present invention is also very suitable for administering active ingredients that combat internal parasites (endo-parasites) such as worms living in the blood or in organs of the animal. Thus, the active ingredient can be an anthelmintic (dewormer).

Anthelmintics (dewormers) are a heterogeneous group of drugs but they are selectively toxic to worms. The drugs can achieve this by either inhibiting the metabolic process vital to the parasite, or by causing the parasite to be exposed to higher concentration of drug than are the hosts cells, which means that one makes use of the existence of an advantageous therapeutic window. Anthelmintics can affect the target parasite during treatment by interfering with the integrity of parasite cells, inhibiting neuromuscular transmission and coordination, or mechanisms which protect against host immunity, that ultimately lead to the starvation, neuromuscular paralysis, death and expulsion of the parasite. Anthelmintics are commonly administered by drench, paste, orally, or by injection. The drugs are absorbed into the blood stream and widely diffused. They are metabolized in the liver and excreted in feces and urine. In the animal health field anthelmintics are used widely used against roundworms, lungworms, tapeworms, intestinal worms, whipworms, hookworms, pinworms, trichinella (trichinosis), and other less common organisms, liver flukes and other less common organisms in a broad range of animals such as beef, cattle, swine, goats, horses, and pets like cats and dogs. The activity spectrum of anthelmintics for dogs and cats embraces Trematodes such as *Alaria alata* and *Opisthorchis tenuicollis*; Cestodes such as *Taenia hydatigena, Taenia pisiformis, Taenia ovis, Hydatigena Taenla taeniaeformis, Echinococcus granulosus, Echinococcus multilocularis, Dipylidium caninum, Diphyliobothrium latum, Multiceps multiceps, Multiceps serialis, Mesocestoides lineatus,* and *Mesocestoides corti*; and Nematodes such as *Ancylostoma caninum, Uncinaria stenocephaia, Toxocara canis, Toxocara cati, Toxascaris leonina, Strongyloides stercoralis, Filaroides osieri, Capillaria aerophila, Capillaria plica, Capillaria hepatica, Trichinella spiralis, Angiostrongylus vasorum, Trichuris vulpis, Spirocerca lupi, Dirofilaria immitis, Ancylostoma tubaeforme,* and *Aelurostrongylus abstrusus.*

Internal parasites within the present invention include all species of worm infestation (helminthes) but also bacteria and viruses causing bacterial and viral infections, in particular those that infest the organs or parts of the body, such as the lungs, heart, alimentary tract or extremities, or which spread through the whole organism.

The anthelmintic can be selected from endo-parasiticides and endecticides including one of the following well-known groups of dewormers such as macrocyclic lactones (sometimes called simply macrolides), benzimidazoles, pro-benzimidazoles, imidazothiazoles, tetrahydropyrimidines, organophosphates and piperazines.

A most preferred group of anthelmintics consists of the more modern natural or chemically modified macrocyclic lactones (macrolides), such as avermectins, milbemycins and derivatives thereof, including prominent representatives such as Ivermectin, Doramectin, Moxidectin, Selamectin, Emamectin, Eprinomectin, Milbemectin, Abamectin, Milbemycin oxime, Nemadectin, and a derivative thereof, in free form or in the form of a physiologically acceptable salt.

The macrocyclic lactones are most preferred because they exhibit a broad spectrum of activity. Most of them exhibit ecto and in parallel endo-parsiticidal activity. Therefore, they are also called endectocides. Macrocyclic lactones bind to glutamated chlorine channels causing in the first instance paralysis and later on the death of the parasite.

In the context of the invention, a preferred group of macrocyclic lactones is represented by compounds of formula (I)

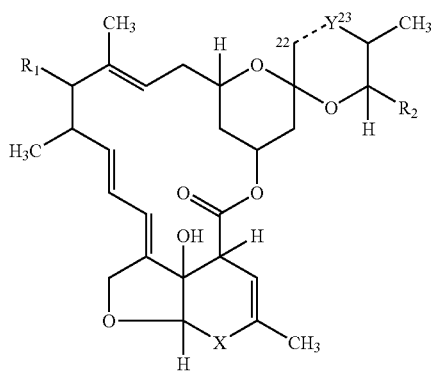

(I)

wherein X is —C(H)(OH)—; —C(O)—; or —C(=N—OH)—; Y is —C(H$_2$)—; =C(H)—; —C(H)(OH)—; or —C(=N—OCH$_3$)—; R$_1$ is hydrogen or one of radicals

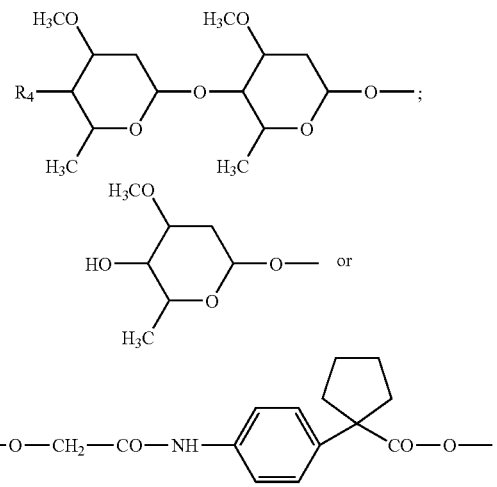

R$_4$ is hydroxyl, —NH—CH$_3$ or —NH—OCH$_3$; R$_2$ is hydrogen, —CH$_3$, —C$_2$H$_5$, —CH(CH$_3$)—CH$_3$, —CH(CH$_3$)—C$_2$H$_5$, —C(CH$_3$)=CH—CH(CH$_3$)$_2$ or cyclohexyl; and if the bond between atoms 22 and 23 represents a double bond the carbon atom in 23-position is unsubstituted so that Y is =C(H)—, or if is the bond between atoms 22 and 23 is a single bond the carbon atom in 23-position is unsubstituted or substituted by hydroxy or by the group =N—O—CH$_3$ so that Y is —C(H$_2$)—; —C(H)(OH)—; or —C(=N—OCH$_3$)—; in free form or in the form of a physiologically acceptable salt.

Typical and especially preferred representatives of compounds of formula (I) are:

1) Ivermectin is 22,23-Dihydroabamectin; 22,23-dihydroavermectin B 1; or 22,23-dihydro C-076B 1, wherein X is —C(H)(OH)—; Y is —C(H$_2$)—; R$_1$ is the radical

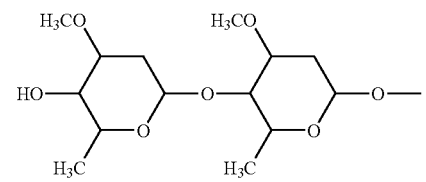 [SMILES: COC1CC(OC)C(OC2CC(OC)C(O)C(C)O2)C(C)O1]

R$_2$ is either —CH(CH$_3$)—CH$_3$ or —CH(CH$_3$)—C$_2$H$_5$ and the bond between atoms 22 and 23 represents a single bond. Ivermectin is known from U.S. Pat. No. 4,199,569.

2) Doramectin is 25-Cyclohexyl-5-O-demethyl-25-de(1-methylpropyl)avermectin A 1a, wherein X is —C(H)(OH)—; Y is =C(H)—; R$_1$ is the radical

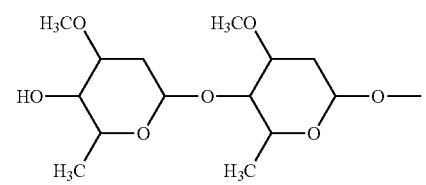 [SMILES: COC1CC(OC)C(OC2CC(OC)C(O)C(C)O2)C(C)O1]

R$_2$ is cyclohexyl and the bond between atoms 22 and 23 represents a double bond. Doramectin is known from U.S. Pat. No. 5,089,480.

3) Moxidectin, is [6 R, 23 E, 25 S (E)]-5-O-Demethyl-28-deoxy-25-(1,3-dimethyl-1-butenyl)-6,28-epoxy-23-

(methoxy imino)milbemycin B, wherein X is —C(H)(OH)—; Y is —C(=N—OCH₃)—; R₁ is hydrogen; R₂ is —C(CH₃)=CH—CH(CH₃)₂; and the bond between atoms 22 and 23 represents a single bond. Moxidectin, is known from EP-0,237,339 and U.S. Pat. No. 4,916,154.

4) Selamectin is 25-cyclohexyl-25-de(1-methylpropyl)-5-deoxy-22,23-dihydro-5-(hydroxyimino)avermectin B1 monosaccharide and thus a compound of formula (I), wherein X is —C(=N—OH)—; Y is —C(H₂)—; R₁ is the radical

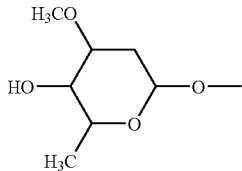

R₂ is cyclohexyl; and the bond between atoms 22 and 23 represents a single bond. Selamectin is known e.g. from: ECTOPARASITE ACTIVITY OF SELAMECTIN; A novel endectocide for dogs and cats. A Pfizer Symposium, held in conjunction with The 17th international Conference of the World Association for the Advancement of Veterinary Parasitology, 19 Aug. 1999. Copenhagen, Denmark.

5) Emamectin is (4primeprime R)-5-O-demethyl-4primeprimedeoxy-4primeprime-(methlamino)avermectin A 1a and (4primeprime R)-5-O-demethyl-25-de(1-methylpropyl)-4primeprime-deoxy-4primeprime-(methylamino)-25-(1-methylethyl)avermectin A 1a (9:1), wherein X is —C(H)(OH)—; Y is =C(H)—; R₁ is

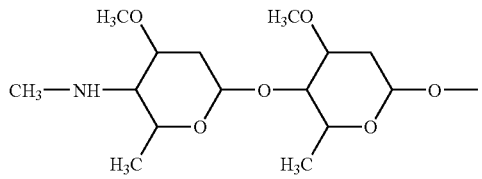

R₂ is —CH(CH₃)—CH₃, or —CH(CH₃)—C₂H₅, and the bond between atoms 22 and 23 represents a double bond. Emamectin is known from U.S. Pat. No. 4,874,749.

6) Eprinomectin is (4primeprime R)-4primeprime-epi-(acetylamino)-4primeprime-deoxyavermectin B 1, wherein X is —C(H)(OH)—; Y is =C(H)—; R₁ is the radical

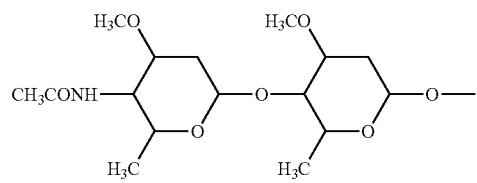

R₂ is —CH(CH₃)—CH₃, or —CH(CH₃)—C₂H₅, and the bond between atoms 22 and 23 represents a double bond. Eprinomectin is known from U.S. Pat. No. 4,427,663.

7) Milbemectin is (6R,25R)-5-O-demethyl-28-deoxy-6,28epoxy-25-methylmilbemycin, wherein X is —C(H)(OH)—; Y is —C(H₂)—; R₁ is hydrogen; R₂ is —CH₃, or —C₂H₅; and the bond between atoms 22 and 23 represents a single bond. Milbemectin is known from U.S. Pat. No. 3,950,360.

8) Abamectin is Avermectin B 1 which is also named 5-O-demethylavermectin A 1a and 5-O-demethyl-25-de(1-methylpropyl)-25-(1-methylethyl)avermectin A 1a (4:1), wherein X is —C(H)(OH)—; Y is =C(H)—; R₁ is the radical

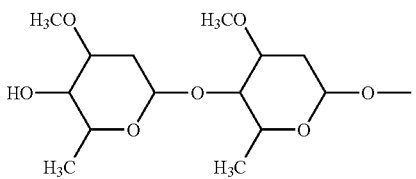

R₂ is —CH(CH₃)—CH₃, or —CH(CH₃)—C₂H₅; and the bond between atoms 22 and 23 represents a double bond. Abamectin is known from U.S. Pat. No. 4,310,519.

9) Milbemycin oxim is milbemycin A 4 5-oxime; milbemycin A 3 5-oxime, wherein X is —C(H)(OH)—; Y is —C(H₂)—; R₁ is hydrogen; R₂ is —CH(CH₃)—CH₃, or —CH(CH₃)—C₂H₅, and the bond between atoms 22 and 23 represents a single bond. Milbemycin oxim is known from U.S. Pat. No. 4,547,520.

10) The compound of the formula (I) wherein X is —C(H)(OH)—; Y is —C(H₂)—; R₁ is the radical

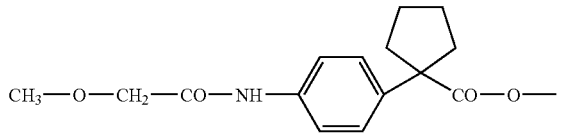

R₂ is —CH₃ or C₂H₅, and the bond between atoms 22 and 23 represents a single bond. This compound is known from WO 01/83500.

11) Nemadectin is antibiotic S-541A; also named [6 R, 23 S, 25 S,(E)]-5-O-Demethyl-28-deoxy-25-(1,3-dimethyl-1-butenyl)-6,28-epoxy-23-hydroxymilbemycin B; wherein X is =CH—OH; Y is —C(H₂)—; R₁ is hydrogen; R₂ is —C(CH₃)=CH—CH(CH₃)₂, and the bond between atoms 22 and 23 represents a single bond. Nemadectin is known from U.S. Pat. No. 4,869,901.

The compounds specifically mentioned under items 1-11 hereinbefore, are preferred embodiments of the present invention and can be used either alone or in combination with another endo-parasiticide, ecto-parasiticide or endecticide.

Benzimidazoles, benzimidazole carbamate and pro-benzimidazoles interfere with energy metabolism by inhibition of polymerization of microtubules and include very potent compounds such as thiabendazole, mebendazole, fenbendazole, oxfendazole, oxibendazole, albendazole, luxabendazole, netobimin, parbendazole, flubendazole, cyclobendazole, febantel, thiophanate and derivatives thereof.

Imidazothiazoles are cholinergic agonists and include highly active compounds such as tetramisole, levamisole, and derivatives thereof.

Tetrahydropyrimidines act are also cholinergic agonists and include highly active compounds such as morantel, pyrantel, and derivatives thereof.

Organophosphates are inhibitors of cholinesterase. This class includes potent compounds such as dichlorvos, haloxon, trichlorfon, and derivatives thereof.

Piperazines exhibit anticholinergic action and block neuromuscular transmission. This class includes highly active compounds such as piperazine and derivatives thereof.

Salicylanilide selected from closantel, tribromsalan, dibromsalan, oxychlozanide, clioxanide, rafoxanide, brotianide, bromoxanide and derivatives thereof.

Within the present invention the anthelmintic (dewormer) a preferred embodiment consist of a combination of a macrocyclic lactone and an anthelmintic selected from the group consisting of Albendazole, Clorsulon, Cydectin, Diethylcarbamazine, Febantel, Fenbendazole, Haloxon, Levamisole, Mebendazole, Morantel, Oxyclozanide, Oxibendazole, Oxfendazole, Oxfendazole, Oxamniquine, Pyrantel, Piperazine, Praziquantel, Thiabendazole, Tetramisole, Trichlorfon, Thiabendazole, and derivatives thereof. Most preferred is Praziquantel. In order to broaden the activity spectrum towards ecto-parasites said anthelmintic combination can contain in addition to the dewormers a parasiticidally effective amount of an insecticide, acaricide or an insecticide and an acaricide. Of course one could also add an antibiotic for treating bacterial disease.

All of the suitable parasiticides mentioned hereinbefore are known. Most of them are described in THE MERCK INDEX 1999 by Merck & Co Inc, Whitehouse Station, N.J., USA; published on CD-ROM by Chapman & Hill/CRC, 1999, Hampden Data Service Ltd. and in the literature specifically mentioned in THE MERCK INDEX 1999.

Suitable antimicrobial active ingredients are, e.g. various penicillins, tetracyclines, sulfonamides, cephalosporins, cephamycins, aminoglucosids, trimethoprim, dimetridazoles, erythromycin, framycetin, fruazolidone, various pleuromutilins such as thiamulin, valnemulin, various macrolides, streptomycin and substances acting against protozoa, e.g. clopidol, salinomycin, monensin, halofuginone, narasin, robenidine, etc.

Behavioral disorders include e.g. separation worry or travel sickness of dogs and cats. A suitable compound acting against behavioral disorders is e.g. clomipramine.

The chewable combination according to the present invention may also contain an active ingredient for the treatment of disfunctions or hypo-activity.

Dysfunction or hypo-activity is understood to include functions like autoimmune disorders, which deviate from the norm, whether through inborn or acquired damage to individual organs or tissue. This complex also includes rheumatic diseases, pathological changes to joints, bones or internal organs, and much more. A prominent representative of compounds that can be used in this complex area is cyclosporine and derivatives thereof. The term "animal disease" even includes different types of cancer and metastasis progression in connective tissues that are common in animals. In this field bisphosphonates like coledronate, clodronate, etidronate, pamidronate and alendronate play an important role. Said bisphosphonates can also be administered in the treatment or prophylaxis of ulcers, rheumatoid arthritis and other arthitides, and periodontitis. Another suitable class of active ingredients encompasses anti-inflammatory agents such as benzenesulfonamides like Deracoxib, which is extremely suitable for the control of pain and inflammation associated with osteoarthritis. Further anti-inflammatory agents are diclofenac and derivatives thereof.

In the present invention, the administration problems depicted in connection with conventional oral dosage forms, like tablets and capsules, can be very easily resolved and chewable products can be prepared, which are taken orally by the animals without causing any problems. The animals actually take the chewable veterinary composition voluntarily.

SUMMARY OF THE INVENTION

The present invention overcomes the disadvantages and shortcomings of the prior art by providing an easy-to-use, safe, powerful, and stable veterinary formulation consisting of a highly palatable ductile chewable veterinary composition which is produced by an extrusion process wherein the product is extruded at or near room temperature, and where the extruder is cooled down below room temperature, preferably to 5-10° C. The palatable ductile chewable composition constitutes a veterinary composition and is administered orally. The composition is capable of killing endo-parasites and ecto-parasites and/or can be used for treating prophylactic or curative animal diseases, and it is useful for the treatment of any warm-blooded non-human animal, including herd animals, like horses, cattle, sheep or poultry and preferably pets like dogs and cats.

The highly palatable ductile chewable veterinary composition of the invention is composed of an organic composition which contains an effective amount of one or more active ingredients, preferably an effective amount of a mono, binary or ternary mixture of organic compounds capable of controlling ecto-parasites, endo-parasites or bacterial of viral pathogens or a combination of ecto-parasites, endo-parasites, bacterial or viral pathogens. Depending on the mode of action the highly palatable ductile chewable veterinary composition of the invention contains a parasiticidally or anti-pathogenically effective amount of one or more active ingredients. The expression "parasiticidally effective amount" refers to that amount of active ingredient in the composition which will fully control the target parasite which means that 95-100%, preferably 98-100% or close to 100% of the parasites are killed and the active ingredient is nevertheless well tolerated. The expression "anti-pathogenically effective amount" refers to that amount of active ingredient in the composition which will efficiently cure a bacterial, viral or behavioral disease or if administered prophylactically will suppress the outbreak of such a disease. The highly palatable ductile chewable veterinary composition of the invention comprises an effective amount of one or more ingredients that are active against animal pests, pathogens or animal diseases; it further comprises meat flavoring and partially gelatinized starch, and it comprises of a softener; and of up to 9% (w/w), preferably 3-7% (w/w), most preferred 4-6% (w/w), of water. It is essential that that during the extrusion process the extruder is cooled down below room temperature. A temperature range of 5-10° C. is ideal.

Each of the following paragraphs defines a preferred embodiment of the present invention:

A highly palatable ductile chewable veterinary composition that comprises (A) an effective amount of one or more ingredients that are active against animal pests, pathogens or animal diseases; (B) meat flavoring; (C) partially gelatinized starch; (D) a softener; and (E) optionally up to 9% (w/w) water.

A highly palatable ductile chewable veterinary composition as defined above capable of controlling endo-parasites and simultaneously ecto-parasites of non-human animals.

A highly palatable ductile chewable veterinary composition as defined above wherein the animal disease comprises bacterial infections, viral infections, behavioral disorders, inflammatory diseases, and auto-immune diseases.

A highly palatable ductile chewable veterinary composition as defined above comprising 20 to 30% (w/w) of a natural meat flavoring.

A highly palatable ductile chewable veterinary composition as defined above wherein the natural meat flavoring comprises 20 to 55% (w/w) fat.

A highly palatable ductile chewable veterinary composition as defined above comprising 25 to 70% (w/w) of partially gelatinized starch.

A highly palatable ductile chewable veterinary composition as defined above wherein the partially gelatinized starch comprises 12 to 17% (w/w) of gelatinized starch.

A highly palatable ductile chewable veterinary composition as defined above comprising 10 to 20% (w/w), preferably about 11-15% (w/w), of a softener, based upon the weight of the partially gelatinized starch.

A highly palatable ductile chewable veterinary composition as defined above wherein the softener is selected from the group consisting of glycerol, polyethylene glycol and polypropylene glycol.

A highly palatable ductile chewable veterinary composition as defined above comprising up to 9% (w/w) preferably 3 to 7% (w/w), more preferably 4 to 6% (w/w) of water.

A highly palatable ductile chewable veterinary composition as defined above comprising 1 to 10% (w/w), preferably 3 to 7% (w/w) of a sweetener.

A highly palatable ductile chewable veterinary composition as defined above comprising 0 to 3.5% (w/w), preferably 0.01 to 0.5% (w/w) of an antioxidant.

A highly palatable ductile chewable veterinary composition as defined above comprising 0 to 5% (w/w), preferably 0.05 to 2% (w/w) of a coloring agent.

A highly palatable ductile chewable veterinary composition as defined above comprising 0 to 4% (w/w) of sodium chloride.

A highly palatable ductile chewable veterinary composition as defined above comprising an parasiticidally effective amount of an ecto-parasiticide, an endo-parasiticide, an endectocide or of a combination of a parasiticide selected from the group consisting of an ecto-parasiticide, an endo-parasiticide and an endectocide.

A highly palatable ductile chewable veterinary composition as defined above wherein the ecto-parasiticide is active against insects, members of the order Acarina or insects and members of the order Acarina.

A highly palatable ductile chewable veterinary composition as defined above wherein the ecto-parasiticide is an insecticide which is either an insect adulticides or insect growth regulators.

A highly palatable ductile chewable veterinary composition as defined above comprising an parasiticidally effective amount of an endo-parasiticide or endectocide selected from the group consisting of macrocyclic lactones, benzimidazoles, pro-benzimidazoles, imidazothiazoles, tetrahydropyrimidines, organophosphates and piperazines.

A highly palatable ductile chewable veterinary composition as defined above comprising an effective amount of a natural or chemically modified macrocyclic lactone of formula (I)

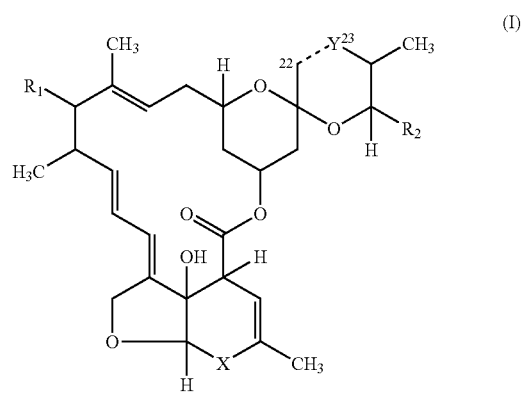

wherein X is —C(H)(OH)—; —C(O)—; or —C(=N—OH)—; Y is —C(H$_2$)—; =C(H)—; —C(H)(OH)—; or —C(=N—OCH$_3$)—; R$_1$ is hydrogen or one of radicals

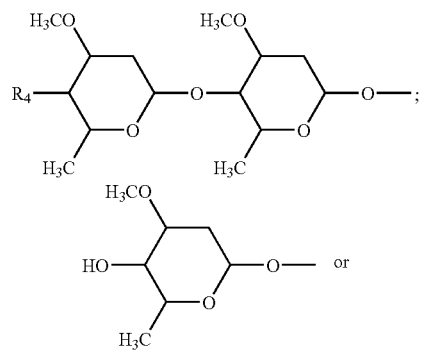

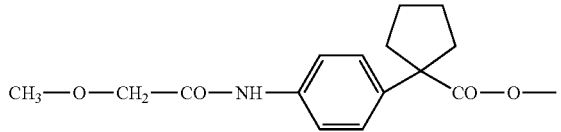

R$_4$ is hydroxyl, —NH—CH$_3$ or —NH—OCH$_3$; R$_2$ is hydrogen, —CH$_3$, —C$_2$H$_5$, —CH(CH$_3$)—CH$_3$, —CH(CH$_3$)—C$_2$H$_5$, —C(CH$_3$)=CH—CH(CH$_3$)$_2$ or cyclohexyl; and if the bond between atoms 22 and 23 represents a double bond the carbon atom in 23-position is unsubstituted so that Y is =C(H)—, or if is the bond between atoms 22 and 23 is a single bond the carbon atom in 23-position is unsubstituted or substituted by hydroxy or by the group =N—O—CH$_3$ so that Y is —C(H$_2$)—; —C(H)(OH)—; or —C(=N—OCH$_3$)—; in free form or in the form of a physiologically acceptable salt.

A highly palatable ductile chewable veterinary composition as defined above comprising an effective amount of a natural or chemically modified macrocyclic lactone of formula (I) wherein X is —C(H)(OH)—; Y is —C(H$_2$)—; R$_1$ is the radical

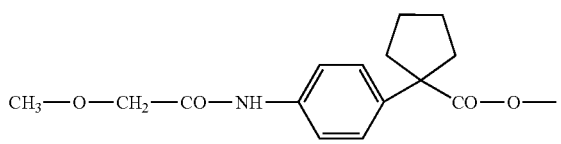

R$_2$ is —CH$_3$ or C$_2$H$_5$, and the bond between atoms 22 and 23 represents a single bond.

A highly palatable ductile chewable veterinary composition as defined above wherein the animal pests are external animal parasites or internal animal parasites or both.

A highly palatable ductile chewable veterinary composition as defined above wherein the macrocyclic lactone is selected from the group consisting of avermectins, milbemycins and derivatives thereof, in free form or in the form of a physiologically acceptable salt.

A highly palatable ductile chewable veterinary composition as defined above wherein the macrocyclic lactone is selected from the group consisting of Ivermectin, Doramectin, Moxidectin, Selamectin, Emamectin, Eprinomectin, Milbemectin, Abamectin, Milbemycin oxime, Nemadectin, and a derivative thereof, in free form or in the form of a physiologically acceptable salt.

A highly palatable ductile chewable veterinary composition as defined above comprising an effective amount of a macrocyclic lactone in combination with an effective amount of an anthelmintic selected from the group consisting of Albendazole, Clorsulon, Cydectin, Diethylcarbamazine, Febantel, Fenbendazole, Haloxon, Levamisole, Mebendazole, Morantel, Oxyclozanide, Oxibendazole, Oxfendazole, Oxfendazole, Oxamniquine, Pyrantel, Piperazine, Praziquantel, Thiabendazole, Tetramisole, Trichlorfon, Thiabendazole, and a derivative thereof.

A highly palatable ductile chewable veterinary composition as defined above comprising additionally an effective amount of an insecticide, acaricide or an insecticide and an acaricide.

A highly palatable ductile chewable veterinary composition as defined above comprising an effective amount of milbemycin oxime and praziquantel.

A highly palatable ductile chewable veterinary composition as defined above comprising an effective amount of lufenuron, praziquantel and milbemycin oxime.

A highly palatable ductile chewable veterinary composition as defined above comprising an effective amount of cyclosporin.

A highly palatable ductile chewable veterinary composition as defined above comprising an effective amount of an antimicrobial selected from the group consisting of a penicillin, tetracycline, sulfonamide, cephalosporin, cephamycin, aminoglucosid, trimethoprim, dimetridazole, erythromycin, framycetin, fruazolidone, pleuromutilin, streptomycin and a compound that is active against protozoa.

A highly palatable ductile chewable veterinary composition as defined above comprising an effective amount of compound that is active against behavioral including separation worry or travel sickness of dogs and cats.

A highly palatable ductile chewable veterinary composition as defined above wherein the active ingredient or a different chemical class is an insecticide or acaricide.

A highly palatable ductile chewable veterinary composition as defined above wherein the insecticide is selected from the group consisting of insect killers and insect growth regulators.

Another preferred embodiment of the present invention is a method of controlling said animal pests or pathogens and of curing or preventing said animal diseases by feeding an animal with said highly palatable ductile chewable veterinary composition.

Yet another preferred embodiment of the present invention is a method of controlling said animal pests or pathogens and of curing or preventing said animal diseases by feeding an animal with said highly palatable ductile chewable veterinary composition.

Yet another preferred embodiment of the present invention is a process for the production of a highly palatable ductile chewable veterinary composition as defined above, comprising (i) feeding the hopper of an extruder with an effective amount of one or more ingredients that are active against animal pests, pathogens or animal diseases; meat flavoring; partially gelatinized starch; a softener; and up to 9% (w/w) of water, (ii) cooling constantly down the mixture of active ingredients and carriers so that the temperature of the extrudate in the extruder does during the whole extrusion process at no time exceed 40° C., (iii) pressing the extrudate through a die that is decisive for the shape of the chewable product, and (iv) cutting the extrudate that leaves the extruder into equal pieces.

Yet another preferred embodiment of the present invention is a process as defined above wherein the hopper of the extruder is fed continuously and simultaneously with pre-mixture (1) and pre-mixture (2), wherein pre-mixture (1) consist of a homogenized mixture of one or more active ingredients and partially gelatinized starch, and pre-mixture (2) consists of a homogenized mixture of meat flavoring, a softener and optionally of a carrier selected from the group consisting of a sweetener, softener, an antioxidant, a coloring agent and sodium chloride.

Yet another preferred embodiment of the present invention is a process as defined above wherein the extruder is cooled down below room temperature.

A further preferred embodiment of the present invention is a method of controlling nonhuman animal pests or nonhuman animal pathogens or of curing or preventing nonhuman animals diseases comprising feeding an animal with a palatable ductile chewable veterinary composition as defined above.

A further preferred embodiment of the present invention is a method as defined above, wherein the palatable ductile chewable veterinary composition consist of one chewable portion containing an effective amount of a compound or mixture of compounds capable of controlling nonhuman animal pests or nonhuman animal pathogens or of curing or preventing nonhuman animals diseases.

A further preferred embodiment of the present invention is a method as defined above, wherein the amount of active ingredient is adjusted to the bodyweight of the nonhuman animal that is in need of the treatment.

Another preferred embodiment of the present invention is the use of (A) an effective amount of one or more Ingredients that are active against animal pests, pathogens or animal diseases; (B) meat flavoring; (C) partially gelatinized starch; (D) a softener; (E) up to 9% water; and an active ingredient suitable for combating animal pests, pathogens or animal diseases for the preparation of a highly palatable ductile chewable veterinary composition.

Another preferred embodiment of the present invention is the use as defined above, comprising 20 to 30% (w/w) of a natural meat flavoring.

Another preferred embodiment of the present invention is the use as defined above, wherein the natural meat flavoring comprises 20 to 55% (w/w) fat.

Another preferred embodiment of the present invention is the use as defined above, comprising 25 to 70% (w/w) of partially gelatinized starch.

Another preferred embodiment of the present invention is the use as defined above, wherein the partially gelatinized starch comprises 12 to 17% (w/w) of gelatinized starch.

Another preferred embodiment of the present invention is the use as defined above, comprising 10 to 20% (w/w) of a softener, based upon the weight of the partially gelatinized starch.

Another preferred embodiment of the present invention is the use as defined above, wherein the softener is selected from the group consisting of glycerol, polyethylene glycol and polypropylene glycol.

Another preferred embodiment of the present invention is the use as defined above, comprising 3 to 7% (w/w) of water.

Another preferred embodiment of the present invention is the use as defined above, wherein the animal pests are external animal parasites or internal animal parasites or both.

Another preferred embodiment of the present invention is the use as defined above, comprising 1 to 10% (w/w) of a sweetener.

Another preferred embodiment of the present invention is the use as defined above, comprising 0 to 3.5% (w/w) of an antioxidant.

Another preferred embodiment of the present invention is the use as defined above, comprising 0 to 5% (w/w) of a coloring agent.

Another preferred embodiment of the present invention is the use as defined above, comprising 0 to 4% (w/w) of sodium chloride.

Another preferred embodiment of the present invention is the use as defined above, comprising an parasiticidally effective amount of an ecto-parasiticide, an endo-parasiticide, an endectocide or of a combination of a parasiticide selected from the group consisting of an ecto-parasiticide, an endo-parasiticide and an endectocide.

Another preferred embodiment of the present invention is the use as defined above, wherein the ecto-parasiticide is active against insects, members of the order Acarina or insects and members of the order Acarina.

Another preferred embodiment of the present invention is the use as defined above, wherein the ecto-parasiticide is an insecticide which is either an insect adulticides or insect growth regulators.

Another preferred embodiment of the present invention is the use as defined above, comprising an parasiticidally effective amount of an endo-parasiticide or endecticide selected from the group consisting of macrocyclic lactones, benzimidazoles, pro-benzimidazoles, imidazothiazoles, tetrahydropyrimidines, organophosphates and piperazines.

Another preferred embodiment of the present invention is the use as defined above, comprising an effective amount of a natural or chemically modified macrocyclic lactone of formula (I)

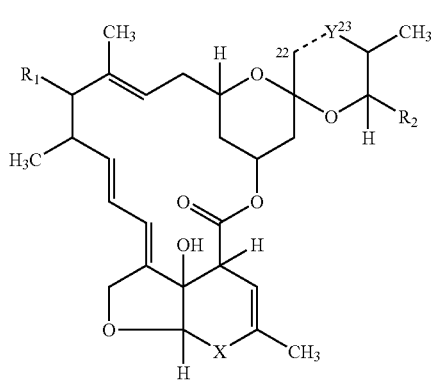

wherein X is —C(H)(OH)—; —C(O)—; or —C(=N—OH)—; Y is —C(H$_2$)—; =C(H)—; —C(H)(OH)—; or —C(=N—OCH$_3$)—; R$_1$ is hydrogen or one of radicals

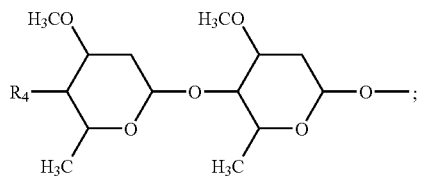

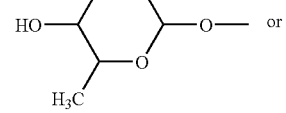

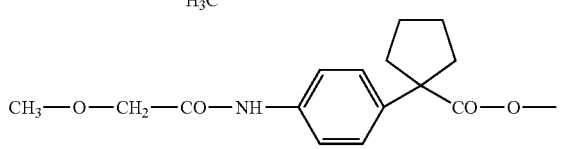

R$_4$ is hydroxyl, —NH—CH$_3$ or —NH—OCH$_3$; R$_2$ is hydrogen, —CH$_3$, —C$_2$H$_5$, —CH(CH$_3$)—CH$_3$, —CH(CH$_3$)—C$_2$H$_5$, —C(CH$_3$)=CH—CH(CH$_3$)$_2$ or cyclohexyl; and if the bond between atoms 22 and 23 represents a double bond the carbon atom in 23-position is unsubstituted so that Y is =C(H)—, or if is the bond between atoms 22 and 23 is a single bond the carbon atom in 23-position is unsubstituted or substituted by hydroxy or by the group =N—O—CH$_3$ so that Y is —C(H$_2$)—; —C(H)(OH)—; or —C(=N—OCH$_3$)—; in free form or in the form of a physiologically acceptable salt.

Another preferred embodiment of the present invention is the use as defined above, wherein the macrocyclic lactone is a compound of the formula (I) wherein X is —C(H)(OH)—; Y is —C(H$_2$)—; R$_1$ is the radical

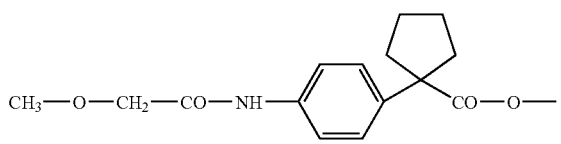

R$_2$ is —CH$_3$ or C$_2$H$_5$, and the bond between atoms 22 and 23 represents a single bond.

Another preferred embodiment of the present invention is the use as defined above, wherein the endecticide is a macrocyclic lactone is selected from the group consisting of avermectins, milbemycins and derivatives thereof, in free form or in the form of a physiologically acceptable salt.

Another preferred embodiment of the present invention is the use as defined above, wherein the macrocyclic lactone is selected from the group consisting of Ivermectin, Doramectin, Moxidectin, Selamectin, Emamectin, Eprinomectin, Milbemectin, Abamectin, Milbemycin oxime, Nemadectin, and a derivative thereof, in free form or in the form of a physiologically acceptable salt.

Another preferred embodiment of the present invention is the use as defined above, comprising an effective amount of a macrocyclic lactone in combination with an effective amount of an anthelmintic selected from the group consisting of Albendazole, Clorsulon, Cydectin, Diethylcarbamazine, Febantel, Fenbendazole, Haloxon, Levamisole, Mebendazole, Morantel, Oxyclozanide, Oxibendazole, Oxfendazole, Oxfendazole, Oxamniquine, Pyrantel, Piperazine, Praziquantel, Thiabendazole, Tetramisole, Trichlorfon, Thiabendazole, and a derivative thereof.

Another preferred embodiment of the present invention is the use as defined above, comprising in addition to an endoparasiticide or an endecticide an effective amount of an insecticide, acaricide or an insecticide and an acaricide.

Another preferred embodiment of the present invention is the use as defined above, comprising an effective amount of milbemycin oxime and praziquantel.

Another preferred embodiment of the present invention is the use as defined above, comprising an effective amount of lufenuron, praziquantel and milbemycin oxime.

Another preferred embodiment of the present invention is the use as defined above, comprising an effective amount of cyclosporin.

Another preferred embodiment of the present invention is the use as defined above, comprising an effective amount of an antimicrobial selected from the group consisting of a penicillin, tetracycline, sulfonamide, cephalosporin, cephamycin, aminoglucosid, trimethoprim, dimetridazole, erythromycin, framycetin, fruazolidone, pleuromutilin, streptomycin and a compound that is active against protozoa.

Another preferred embodiment of the present invention is the use as defined above, comprising an effective amount of compound that is active against behavioral including separation worry or travel sickness of dogs and cats.

An additional preferred embodiment of the present invention is the use of a highly palatable ductile chewable veterinary composition as defined above in a process of controlling nonhuman animal pests or nonhuman animal pathogens or of curing or preventing nonhuman animals diseases.

DETAILED DESCRIPTION OF THE INVENTION

Even so meat flavoring is actually not the main component of the highly palatable ductile chewable veterinary composition it plays the major role for the present invention. It has surprisingly been recognized that the desired high palatability that is necessary for achieving reliable and well-reproducible results strictly depends on the amount of meat flavoring in the final composition. The meat flavoring is either a natural product consisting of dried powdered meat derived, for example, from domestic animals and productive livestock, e.g. pigs, horses, cattle, sheep, goats and poultry including chicken, duck, goose and turkey. It further surprisingly turned out that the natural content of fat in said natural meat powder of 20-55% (w/w) is very important not only for achieving the desired high palatability and excellent taste for the animal but also for achieving the desired softness of the final chewable product. In context with the present invention, a "meat flavoring" shall refer to natural dried and powdered meat as well as to artificial meat flavorings, which are well-known from the food industry. It has however be recognized that artificial meat flavorings are only suitable for the present invention if they already contain 20-55% (w/w) fat or if this amount of fat is added to the artificial flavoring. Fat that can be added to artificial meat flavorings can be chosen either from animal fats or preferably from plant fats including vegetable oils. However, if vegetable oils are used it is advantageous to use hardened/saturated oils. Unsaturated oils are usually liquid at room temperature and result in products that do not show the desired ductility/softness. They are usually too soft. Preferred is the use of saturated/hardened oils/fats that are generally solid at room temperature and lead to chewable compositions showing the desired ductility.

Fats and oils contain many different fatty acids which affect the body in varying ways. Most simply, they are classified as saturated or unsaturated. Saturated fats sometimes are also called hardened fats. It is the saturated fat found in many animal products. Saturated fats are gene rally solid at room temperature. They are mainly of animal origin but can also be isolated from plants. Typical examples stemming from plants are cocoa butter and coconut and palm oils. These products are often used in store-bought baked goods, non-dairy whipped toppings, cream substitutes, most peanut butter and some margarines. Typical sources of saturated fat are: Animal Fat; Coconut Oil; Meat Fat; Bacon Fat; Cream; Palm Kernel Oil; Beef Fat; Palm Oil; Butter; Ham Fat; Pork Fat; Chicken Fat and Skin, Hardened Fat or Oil; Turkey Fat and Skin; Hydrogenated Vegetable Oil; Cocoa Butter; Lamb Fat; and Coconut.

Natural and artificial meat flavoring is commercially obtainable from various producers. Natural Meat Flavoring is, for Example, Obtainable from:

IDF (International Dehydrated Food) INTERNATIONAL DEHYDRATED FOODS, INC. P.O. Box 10347 Springfield, Mo. 65808, USA 800/641-6509 or 417/881-7820

ADF (American Dehydrated Food), American Dehydrated Foods, Inc., P.O. Box 4087 3801 East Sunshine, Springfield, Mo. 65809

IFF (International Flavour and Fragrance), IFF Global Headquarters, 521 West 57th Street, New York, N.Y. 10019, United States Proliant, Proliant Inc.—U.S. Office, 2325 North Loop Drive Ames, Iowa 50010 USA Some example of sources of artificial meat flavoring are:

Kemin, Worldwide Headquarters ● 2100 Maury Street, Box 70 * Des Moines, Iowa 50301-0070 USA.

McCormick, 226 Schilling Circle Hunt Valley, Md. 21031

Givaudan, Givaudan Flavors Corp. (Flavours creation, sales & production) 1199 Edison Drive Cincinnati, Ohio 45216

Haarman und Reimer

Within the present invention the expression "soft" is used to characterize a product that is not as hard and crunchy as, for example, a cornflake and on the other hand is not as ductile as, for example, a marshmallow. The desired ductility/hardness lies somewhere in between. If measured with a commercially available TEXTURE ANALYSER that is commercially available from Stable Micro Systems (TA-XT2 iHR/25), the texture (softness/hardness) of the chewables lies ideally between 6-12 N.

Hard and crunchy products are especially disadvantageous if one intends to treat older dogs and cats because most of these old animals suffer from periodontal disease (Pyorrhea). This disease involves the inflammation and degeneration of tissues that surround and support the teeth. These include the gingiva, alveolar bone, periodontal ligament, and cementum. Periodontitis or the loss of supporting bone is the latest stage of this progressive disorder and is the major cause of tooth loss in old dogs and cats. Animals suffering from periodontitis avoid eating hard and crunchy products because they cause them pain.

The second important feature of the present invention is the use or partially gelatinized starch. This starch contains 10-20% (w/w), preferably about 13-17% (w/w), most preferably 13-17% (w/w) pre-gelatinized starch. This is important as non-gelatinized and completely pre-gelatinized starch do not result in the desired ductility of the final product.

Starches exhibit thermal stability to about 121° C. Starches are carbohydrates of a general formula $(C_6H_{10}O_5)n$ and are derived from corn, wheat, oats, rice, potatoes, yucca and similar plants and vegetables. They consist of about 27% linear polymer (amylose) and about 73% branched polymer (amylopectin). The two polymers are intertwined within starch granules. Granules are insoluble in cold water, but soaking in hot water or under steam pressure ruptures their covering and the polymers hydrate into a colloidal suspension. This product is a pregelatinized starch and has been used in muds for many years. Thus, pregelatinized starch is water-soluble starch that has undergone irreversible changes by heating in water or steam. Many suitable pregelatinized starches are commercially available. For example, Naster® Instant which is a pregelatinized Pea Starch with a high gel strength. Due to its high amylose level, it has some remarkable properties. It shows an excellent stability to high temperatures, shearing and to variations in pH and is ideal for use in cold processes.

A further important component is the softener, which keeps the moisture within the composition and allows to store the final product for weeks and months. It does not become hard and does not dry out.

If the mentioned meat flavoring, partially gelatinized starch and the basic component containing the active ingredient does not contain moisture one should add water during the extrusion process. This has an impact on the flexibility on the chewable veterinary composition of the present invention. It turned out that it is advantageous to adjust the moisture content of the product so that the final product contains water at a concentration equal to or lower than 9% (w/w), preferably about 3 to 7% (w/w), more preferably 4 to 6% (w/w).

For the present invention not only the proportion of meat flavoring and partially pre-gelatinized starch is extremely important but also the production process as such has an influence on the final product. The highly palatable ductile chewable veterinary composition of the present invention is the outcome of a special extrusion process. As such, extrusion is a very common thermoforming process widely used in the food industry for the production of customary feed pellets. However, in order to achieve the chewables according to the present invention, i.e. a highly palatable ductile product one has to modify the process and secure that the extrudate is not heated during the whole extrusion process because this leads to hard and crunchy products, to losses of active ingredient, and especially to a decrease of the palatability. Actually, production in the desired manner can easily be achieved. The highly palatable ductile chewable veterinary composition of the present invention is conveniently carried out in an injection molding machine or extruder. A mixture comprising an effective amount of one or more ingredients that are active against animal pests, pathogens or animal diseases; meat flavoring; partially gelatinized starch; a softener; and up to 9% (w/w) of water is fed through the hopper onto a rotating, reciprocating screw. The material moves along the screw towards the tip. During this process, its temperature is cooled down constantly by means of external coolers around the outside of the barrel and by the shearing action of the screw. The cooling process is controlled so that the temperature of the extrudate during the whole extrusion process does not exceed peak temperature of 40° C. Starting in the feeding zone and continuing in the compression zone, the extrudate should not reach temperatures higher than said 40° C. It has been found that ideally the product is extruded at or near room temperature, and the extruder is cooled down below room temperature, preferably to 5-10° C.

It is then conveyed through the metering zone, where homogenization occurs, to the end of the screw. The homogenized material at the tip is then pressed through a form-determining die to obtain shaped articles of the desired size. The simplest way is cutting the extrudate that leaves the extruder into equal pieces of the desired size. 'Desired' means that each piece contains the appropriate amount of active ingredient. Thus, for example, for big dogs one would produce bigger pieces than for young cats. The amount of active ingredient has to be adapted to the bodyweight of the animal that has to be treated.

This cooling during the extrusion process is extremely important because extruding this kind of a material without cooling can easily lead to temperatures inside the extruder in the range of 100-200° C. High extrusion temperatures however transform the matrix of the extrudate in an undesirable manner. The reason for this being that the starch is heated above the melting and glass transition temperatures of its components so that they undergo endothermic transitions. As a consequence a melting and disordering of the molecular structure of the starch granules takes place, so that an essentially destructurized starch is obtained. Instead of a ductile and rather soft product one obtains a hard or crunchy product which is not only refused by the animals but does not contain a reproducible amount of active ingredient. Many active ingredients are not even stable enough at these relatively high temperatures and are at least partially degraded. As a result the biological activity of the product is reduced, and undesired degradation products can be formed that can cause undesired side effects or lead to allergic reactions. Cooling the extruder to temperatures near room temperature, preferably to 5-10° C., suppresses all these undesired effects and leads to a perfect product that is not only highly palatable but can surprisingly be stored for months without being degraded.

The highly palatable ductile chewable veterinary composition of the present invention may also contain a sweetener for further improving the palatability. Any natural sugar can be used including confectioners sugar, maltitol, xylitol, sorbitol, mannitol, lactose, dextrose, saccharose, glucose or fructose, or any mixture thereof. In addition, artificial sweeteners known in the art, including saccharin, aspartame and Acesulfame-K, may also be used. The sweetener is preferably present in an amount of from 1 to 10% (w/w), preferably between from about 3 to about 7% (w/w) based on the sweetening power of sucrose. The sweetener serves as a palatability enhancer due to its organoleptic properties. Enhancement of the palatability can be especially achieved in those cases where the active ingredient is extremely bitter or exhibits a taste that is absolutely not accepted by the animal.

The veterinary composition of the present invention may also contain an antioxidant even so it turned out that in most of the cases this is not necessary. However, in certain cases the antioxidant serves as a preservative which increases the stability of ingredients that are not stable if exposed for a longer period of time to oxygen. The term "antioxidant" represents the three groups of antioxidants, true antioxidants, such as Tenox 2, Tenox PG, Tenox s-1, BHA (2-t-butyl-4-methoxyphenol), and BHT (2,6-di-t-butyl-4-methylphenol), sodium metabisulfite reducing agents and antioxidant synergists, such as tocopherols (alpha, beta, or delta-tocopherol, tocopherol esters, alpha-tocopherol acetate), alkyl gallates, butylated hydroxyanisole, butylated hydroxytoluene, citric acid, edetic acid and its salts, lecithin and tartaric acid. Further suitable antioxidants are resveratrol, quercetin, benzoic acid, Trolox (N-acetylcysteine, 6-hydroxy-2,5,7,8-tetramethylchroman-2-carboxylic acid), dimethyl thiourea (DMTU), hesperetin, tetrahydrocurcumin, tetrahydrodemethoxycurcumin, and monothioglycerol. Said antioxidant being added in concentrations ranging from 0 to 3.5% (w/w), preferably 0.01 to 0.5% (w/w). Preferred antioxidant are Tenox 2 and BHA (2-t-butyl-4-methoxyphenol).

Sodium chloride may also be added, up to about 4% (w/w), to further improve the palatability of the product and to bind moisture. For certain animals sodium chloride serves like a palatability enhancer.

The highly palatable ductile chewable veterinary composition of the present invention further may contain a softener. The softener for use in the invention serves as a humectant which enhance the flexibility of the pet chew and retains moisture so that the texture of the pet chew is maintained at ambient temperatures. Typically, the softener is present in the highly palatable ductile chewable veterinary composition of the present invention at concentrations from about 10-20% (w/w) and preferably about 11-15% (w/w) based upon the weight of the partially gelatinized starch. Suitable softeners include alcohols such as sorbitol, mannitol, hexanol, pentanol and polyols (such as glycerine, propylene glycol, polyethylene glycol, and polypropylene glycol).

The highly palatable ductile chewable veterinary composition of the present invention may further contain a coloring agent that lead to a better-looking product. The coloring agent can be selected from the group of azo dyes, organic or inorganic pigments, or coloring agents of natural origin, preferably from oxides of iron of titanium. Said coloring agent being added in concentrations ranging from 0 to 5% (w/w), preferably 0.05 to 2% (w/w). A preferred coloring agent is ferric oxide, that is normally used in an amount around 0.1% (w/w).

Technical Equipment

The extruder used for the production of the chewables according to the present invention is a co-rotating twin screw extruder type BCTG-62/28D with a screw diameter of 62 mm and a screw length of L/D ratio of 28D with a pelleting device from Bühler AG; Industriestrasse; CH-9240 Uzwil; Switzerland. The feeder (delivering the dry blend into the extruder) is obtainable from K-Tron, Switzerland. It is a loss in weight feeder: type K2-ML-T 35 twin screw feeder equipped with a AC (twin auger) screw. In addition two pumps are use to deliver glycerin and water separately. In addition, two chillers are used to maintain an extruder temperature below 10° C.

Measurement of the Softness/hardness of the Chewables

The texture (softness/hardness) of the chewy is measured by using a TEXTURE ANALYSER type: TA-XT2 iHR/25 that is commercially available from Stable Micro Systems Ltd. (Headquater: Stable Micro Systems Ltd., Vienna Court, Lammas Road; UK). One measures the peak force (in N) necessary to push a sphere with a velocity of 1 mm/sec to penetrate 2 mm into the chewable. The sphere has a diameter of 8 mm. The texture of the chewables is measured to determine when the chewables are hard enough to be packaged into bins, before they are packaged into blisters. Texture after 24 hours: Typical values lay between 8 and 20 N.

EXAMPLES

Example 1

2-Way-formulation Containing Milbemycin Oxime and Praziguantel

|  | Amount | Percentage [w/w] |
|---|---|---|
| Ingredients |  |  |
| Active ingredient No. 1 Milbemycin oxime | 1.975 kg | 0.395% |
| Active ingredient No. 2 Praziquantel | 19.000 kg | 3.800% |
| Excipients |  |  |
| Pre-gelatinized starch | 205.025 kg | 41.005% |
| Natural chicken flavor | 150.000 kg | 30.000% |
| Sugar | 25.000 kg | 5.000% |
| Sodium chloride powder | 7.500 kg | 1.500% |
| Ferric oxide | 0.500 kg | 0.100% |
| Total solids | 409.000 kg | 81.800% |
| Water | 20.000 kg | 4.000% |

-continued

|  | Amount | Percentage [w/w] |
|---|---|---|
| Glycerin | 70.000 kg | 14.000% |
| Tenox 2 | 1.000 kg | 0.200% |
| Total liquids | 91.000 kg | 18.200% |
| Total batch size | 500.000 kg | 100.000% |

The 2-Way-formulation Containing Milbemycin Oxime and Praziquantel is Produced as Follows:
1. Pre-blend-Milbemycine oxime (1.975 kg) and iron oxide (500 kg) with 13 kg of pre-gelatinized Starch using a V-blender for 5 min.
2. Vacuum transfer through a 10 mesh screen into a bin blender
3. Vacuum transfer praziquantel, confectionery sugar, sodium chloride, chicken flavor and the rest of pregelatinized starch through a 10 mesh screen into a bin blender and blend for 20 min
4. Weigh water into the water tank and weigh glycerin into the glycerin tank and mix with tenox.
5. Start extruder:
6. Cooling unit temperature is set at 5° C.
7. Dry blend (mixture of step 3) is fed into BCTG extruder through K-tron feeding device.
8. Glycerin/Tenox 2 mixture is pumped into the extruder
9. Water is pumped into the extruder
10. Extruder velocity (rpm) is adjusted according feeding velocity of the dry blend
11. Cutting device of the extruder is adjusted to get the appropriate weights of the chewables
12. After extrusion the chewables are transported via conveyer to a hopping conveyer and finally
13. Filled into boxes of not more than 3 inches
14. Curing of the chewables for approx. 24 hours at ambient temperature and relative humidity <60%.
15. After curing chewables are packaged into blister packages
Extruder settings for the different chewy sizes of 0.6 g, 1.5 g, 3.0 g and 6.0 g

| Weights [g] | dry blend feed rate [kg/h] | glycerin addition [kg/h] | water addition [kg/h] | Extruder [rpm] | cutting speed |
|---|---|---|---|---|---|
| 0.6 | 120 | 20.52 | 5.76 | 85 | 2200 |
| 1.5 | 140 | 23.94 | 6.72 | 100 | 2000 |
| 3.0 | 170 | 29.07 | 8.16 | 120 | 1250 |
| 6 | 200 | 34.2 | 9.6 | 140 | 700 |

Example 2

3-Way-formulation Containing Milbemycin Oxime, Praziguantel and Lufenuron

|  | Amount | Percentage [w/w] |
|---|---|---|
| Ingredients |  |  |
| Active ingredient No. 1 Milbemycin oxime | 1.975 kg | 0.395% |
| Active ingredient No. 2 Praziquantel | 19.000 kg | 3.800% |
| Active ingredient No. 3 Lufenuron | 38.340 kg | 7.667% |

-continued

| | Amount | Percentage [w/w] |
|---|---|---|
| Excipients | | |
| Pre-gelatinized starch | 159.690 kg | 31.938% |
| Powdered Cooked Beef | 142.000 kg | 30.000% |
| Stock Aid Bacon Flavour | 25.000 kg | 5.000% |
| Sugar | 25.000 kg | 5.000% |
| Sodium chloride powder | 7.500 kg | 1.500% |
| Ferric oxide | 0.500 kg | 0.100% |
| Total solids | 419.000 kg | 83.800% |
| Water | 20.000 kg | 4.000% |
| Glycerin | 60.000 kg | 12.000% |
| Tenox 2 | 1.000 kg | 0.200% |
| Total liquids | 81.000 kg | 16.200% |
| Total batch size | 500.000 kg | 100.000% |

The 3-Way-formulation containing Milbemycin oxime, Praziquantel and Lufenuron is produced along the same lines as described for the 2-Way-formulation in Example 1.

Example 3

1-Way-formulation Containing Cyclosporin

| Ingredients | Amount | Percentage [w/w] |
|---|---|---|
| Active ingredient | | |
| Cyclosporin | 43.40 g | 8.7% |
| Pre-gelatinized starch | 183.60 g | 36.7% |
| Natural chicken flavor | 150.00 g | 30.0% |
| Sugar | 25.0 g | 5.0% |
| Ferric oxide | 0.50 g | 0.1% |
| Total-solids | 410.00 g | 82.0% |
| Water | 20.00 g | 4.0% |
| Glycerin | 70.00 g | 14.0% |
| Total liquids | 90.00 g | 18.0% |
| Total batch size | 500.00 g | 100.00% |

The 1-Way-formulation containing Cyclosporin is produced along the same lines as described for the 2-Way-formulation in Example 1.

Example 4

Palatability (Acceptance) Test for Different Flavored Chewables of a 3-Way Formulation with 100 Dogs and 100 Cats 100 male and female dogs of different breeds and age are tested. The dogs are divided in 4 groups of 25 dogs of the same bodyweight. The testing person offers once a day to each dog one test-chewable which is adapted to the bodyweight of the dog. In a first instance the chewable is offered by hand for 60 seconds. If the dog does not take the formulation it is offered the dog in his empty bowl. The dog has again 60 seconds to take the formulation, if not, it is paced in his/her mouth. If the dog/cat spits it out it is reported as not accepted. In general not more than 5 to 6 different formulations are tested on consecutive days. Each formulation is packaged separately and labeled so that they can be clearly identified. An analogous test is carried out with 100 cats.

| Chewable to be tested | Flavor | Total acceptance (dogs) [%] |
|---|---|---|
| 2-Way-formulation containing Milbemycin oxime and Praziquantel | Natural bacon | 96 |
| 3-Way-formulation containing Milbemycin oxime, Praziquantel and Lufenuron | Natural bacon | 93 |
| 3-Way-formulation containing Milbemycin oxime, Praziquantel and Lufenuron | Natural beef | 94 |
| 3-Way-formulation containing Milbemycin oxime, Praziquantel and Lufenuron | Natural chicken | 95 |
| 3-Way-formulation containing Milbemycin oxime, Praziquantel and Lufenuron | Artificial bacon | 94 |
| 3-Way-formulation containing Milbemycin oxime, Praziquantel and Lufenuron | Artificial beef | 95 |

The analogues test in cats shows results in absolutely the same range.

Example 5

Stability Tests

Samples of the highly palatable ductile chewable veterinary composition of the present invention are tested for stability under stressing conditions in order to simulate different temperatures and humidity conditions. The samples are tested at 25° C./60 rh, 30° C. 60% rh and 40° C. 75% rh. They are kept in incubators and are analyzed after 3, 6, 9 and 12 months with regard to active ingredient content. The analyze of the content of active ingredient of all samples tested at 25° C./60 rh and 30° C. 60% rh for 12 months show no difference in comparison with identical samples kept in the refrigerator at −25° C. for the same period of time. Chewables kept 12 months at 40° C./75% rh show also good stability results which indicate that they would lead to a shelf live for at least 12 months if stored under normal conditions, i.e. 25° C. or 30° C. and 40-70% rh. No significant difference is seen with regard to the stability of 2-way-formulations containing Milbemycin oxime and Praziquantel and 3-way-formulation containing Milbemycin oxime, Praziquantel and Lufenuron.

What is claimed is:

1. A method for the production of a highly palatable ductile chewable veterinary composition which is an extrudate, said method comprising: (i) feeding the hopper of an extruder with an effective amount of one or more ingredients that are active against animal pests, pathogens or animal diseases; wherein the one or more ingredients comprises milbemycin oxime; natural meat flavoring; about 25 to about 70% (w/w) of partially gelatinized starch, wherein said partially gelatinized starch comprises about 12 to about 17% (w/w) of gelatinized starch; a softener; and up to about 9% (w/w) of water, (ii) cooling the extruder to a temperature below room temperature so that the temperature of the extrudate that leaves the tip of the extruder during the extrusion process does not exceed 40° C., (iii) pressing the extrudate through a die that is decisive for the shape of the chewable product, and (iv) cutting the extrudate that leaves the extruder into equal pieces.

2. The method according to claim 1 wherein the hopper of the extruder is fed continuously and simultaneously with pre-mixture (1) and pre-mixture (2), wherein pre-mixture (1) comprises a homogenized mixture of the one or more active ingredients comprising milbemycin oxime and the partially gelatinized starch, and pre-mixture (2) comprises a homogenized mixture of the natural meat flavoring, the softener and optionally of a carrier selected from the group consisting of a sweetener, a softener, an antioxidant, a coloring agent and sodium chloride.

3. The method according to claim 1 wherein the extruder is cooled down to a temperature of 5-10°.

4. The method according to claim 1, wherein the chewable veterinary composition comprises at least 20% (w/w) of a natural meat flavoring.

5. The method according to claim 4, wherein the natural meat flavoring comprises 20% to 55% (w/w) fat.

6. The method according to claim 1, wherein the chewable veterinary composition comprises 10% to 20% (w/w) of a softener, based upon the weight of the partially gelatinized starch.

7. The method according to claim 6, wherein the softener is selected from the group consisting of glycerol, polyethylene glycol and polypropylene glycol.

8. The method according to claim 1, wherein the chewable veterinary composition comprises 4% to 6% (w/w) of water.

9. The method according to claim 1, wherein the one or more ingredients that are active against animal pests, pathogens or animal diseases further comprises an effective amount of praziquantel.

10. The method according to claim 1, wherein the one or more ingredients that are active against animal pests, pathogens or animal diseases further comprises an effective amount each of lufenuron and praziquantel.

11. The method of claim 6 wherein the softener is an alcohol or a polyol.

12. The method of claim 11 wherein the alcohol is selected from the group consisting of sorbitol, mannitol, hexanol and pentanol.

13. The method of claim 11 where in polyol is selected from the group consisting of glycerine, propylene glycol, polyethylene glycol and polypropylene glycol.

* * * * *